United States Patent [19]

Weisman

[11] 3,948,250
[45] Apr. 6, 1976

[54] PHYSIOLOGICAL INFORMATION DISPLAY
[75] Inventor: Sumner Weisman, Framingham, Mass.
[73] Assignee: Becton, Dickinson and Company, East Rutherford, N.J.
[22] Filed: Sept. 16, 1974
[21] Appl. No.: 506,246

[52] U.S. Cl. .................. 128/2.06 F; 128/2.05 T
[51] Int. Cl.² .................................. A61B 5/04
[58] Field of Search ...... 128/2.05 P, 2.05 R, 2.05 T, 128/2.06 A, 2.06 F, 2.06 R

[56] References Cited
UNITED STATES PATENTS

| | | | |
|---|---|---|---|
| 3,144,019 | 8/1964 | Haber | 128/2.06 A |
| 3,608,545 | 9/1971 | Novack et al. | 128/2.06 F |
| 3,646,930 | 3/1972 | Patterson et al. | 128/2.06 F |
| 3,717,140 | 2/1973 | Greenwood | 128/2.06 F |

Primary Examiner—William E. Kamm
Attorney, Agent, or Firm—Kane, Dalsimer, Kane, Sullivan and Kurucz

[57] ABSTRACT

A physiological function monitor module is provided. The module comprises a physiological function rate detector circuit adapted to receive an input from a patient and convert the same to a DC voltage output signal proportional to the rate of the physiological function of the patient under consideration. The module further includes an alarm generator connected to the output of the detector circuit. The alarm generator includes means for comparing the DC voltage level of the detector circuit to a preselected level and for generating an alarm signal in the event the DC level deviates beyond permissible bounds from the preset level. The module also includes a digital display and an analog/digital converter connected to the output of the detector circuit in driving relationship with the digital display. A character generator is connected to the output of the alarm generator and is also connected in driving relationship to the digital display in parallel with the analog/digital converter. The character generator drives the digital display to produce mnemonics (such as HI, LO, OFF, etc.) which alternately flash with the digital readout on the display in the event of an alarm situation.

4 Claims, 4 Drawing Figures

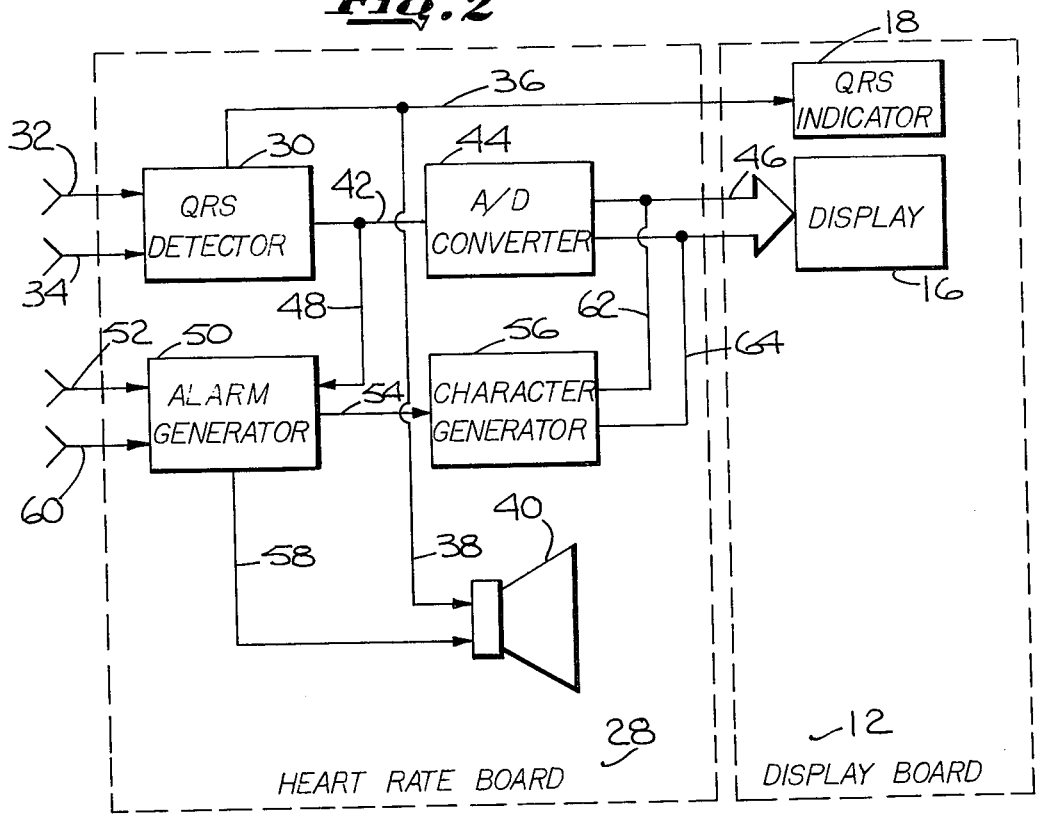
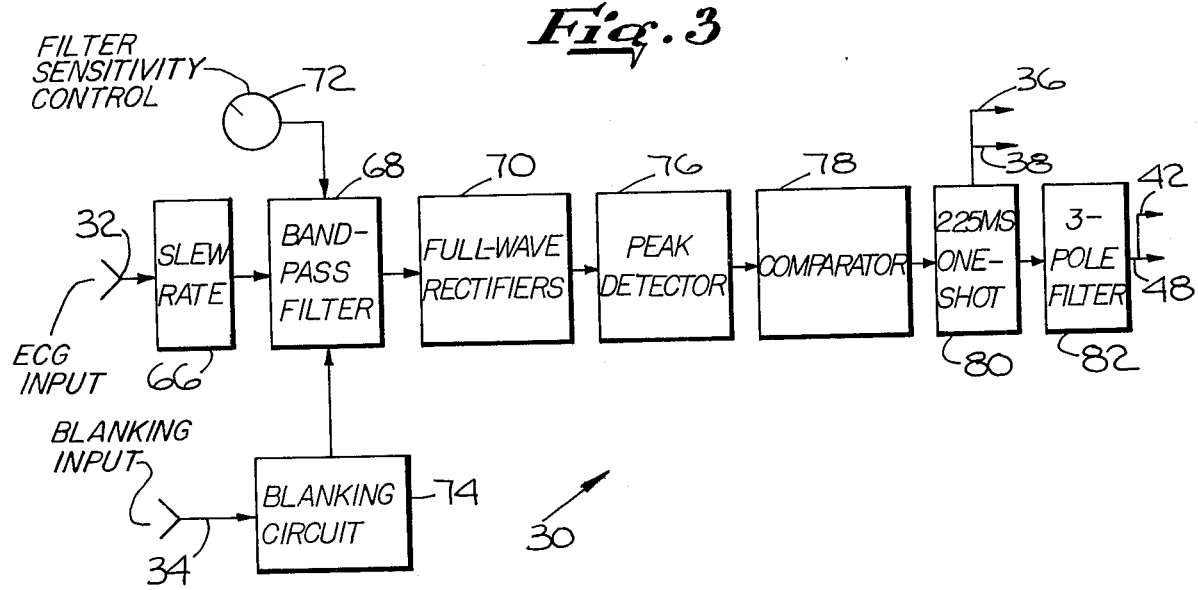

PHYSIOLOGICAL INFORMATION DISPLAY

BACKGROUND OF THE INVENTION

The present invention relates to a physiological monitoring device including means for generating an alarm signal in the event the physiological function rate falls above or below preset limits and for displaying the alarm condition.

Electronic equipment has been used to monitor the physiological body functions of a patient such as in the intensive care facility of hospitals. The body functions may, for example, comprise diastolic and mean blood pressures, heart rate, and the like. It has also been known to provide such units with integral alarm circuits so that in the event the physiological function deviates from preset bounds, an alarm is activated.

Heretofore, upon activation of such an alarm, it has been the duty of the medical attendant to scrutinize the monitor device closely and to make a determination of what change in the physiological function triggered the alarm. In most instances, this may be determined by noting the illumination of small front panel lamps. However, this requires that the attendant return to the instrument and note the meter reading and lamp status, to determine whether the alarm was triggered as a result of too high or too low a reading.

In addition, it is possible for an alarm to be triggered by one extreme and thereafter fall to a completely opposite extreme before the attendant has an opportunity to view the display. For example, in a case where the patient's heartbeat rate is being monitored his condition could be such that the heartbeat rate changes from an overly high rate situation (ventricular tachycandin) to an overly low rate situation (cardiac arrest) in a very short period of time before an attendant would have an opportunity to view and analyze the display. The attendant viewing the display at the time of cardiac arrest would, probably, have no way of knowing that the cardiac arrest was preceded by a high rate situation.

In view of the above, it is the principal object of the present invention to provide a physiological function display device adapted to not only indicate the numerical value of the physiological function at any time but also to indicate whether the value exceeds or falls below preselected limits in an error-proof and extremely visible manner.

A further object is to provide such a device with memory capabilities so that in the event an alarm is triggered, the condition which first triggered the alarm is preserved whether the function returns to a normal condition or even swings to the opposite extreme.

SUMMARY OF THE INVENTION

In accordance with the present invention the above and other beneficial objects and advantages are attained by providing a physiological function monitor module comprising a physiological function rate detector circuit adapted to receive an input from a patient and convert the same as a DC voltage output signal proportional to the rate of the physiological function of the patient under consideration. The module further includes an alarm generator connected to the output of the detector circuit. The alarm generator includes means for comparing the DC voltage level of the detector circuit to a preselected level and for generating an alarm signal in the event the DC level deviates beyond permissible bounds from the preset level. The module also includes a digital display and an analog/digital converter connected to the output of the detector circuit in driving relationship with the digital display. A character generator is connected to the output of the alarm generator and is also connected in driving relationship to the digital display and parallel with the analog/digital converter. The character generator drives the digital display to produce mnemonics (such as HI, LO, OFF, etc.) which alternately flash with the digital readout on the display in the event of an alarm situation. Thus, both the alarm condition and patient data can be readily determined with no chance of operator error.

BRIEF DESCRIPTION OF THE DRAWINGS

In the accompanying drawings:

FIG. 2 is a simplified overall block diagram of the present module;

FIG. 3 is a more detailed block diagram of the detector block of FIG. 2; and,

DETAILED DESCRIPTION OF THE PREFERRED EMBODIMENT

Figure 1:
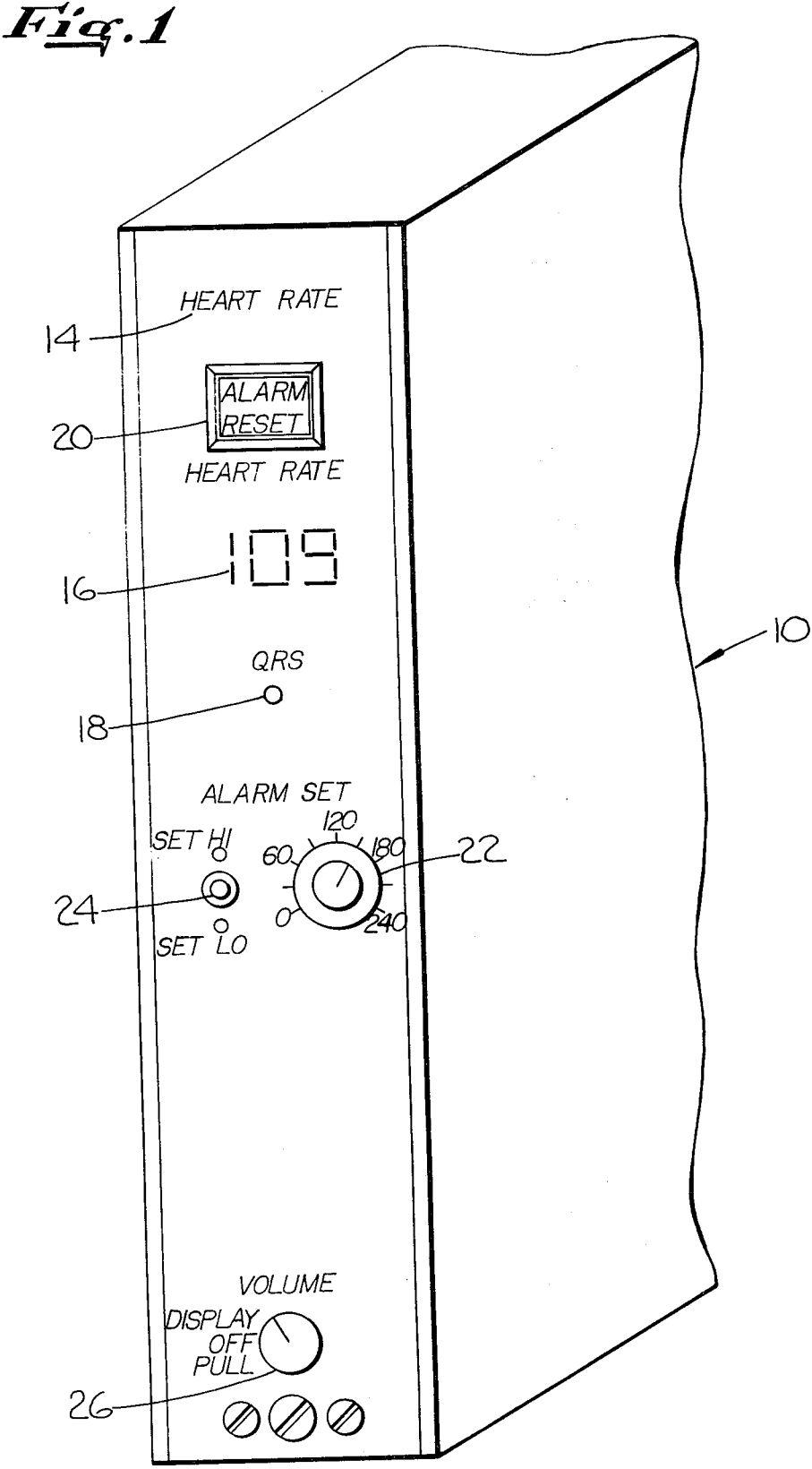
FIG. 1 is a fragmentary perspective view of a physiological function monitor module in accordance with the present invention depicting the front control panel of the unit.

The present invention is illustrated in the accompanying drawings wherein similar components bear the same reference numeral throughout the several views. In the following description, the present invention is described in the context of a heart rate monitor. It should be realized and readily apparent to those familiar with the art that the identical or similar technology could readily be used for monitoring some other desired physiological function such as blood pressure, respiration, or the like.

In FIG. 1, the front panel of a monitoring module 10 in accordance with the present invention is disclosed. The function monitor front panel 12 bears a title 14 ("Heart Rate") indicating the body function being monitored which, in this case, is the heart rate. In addition, the front panel includes a 3-digit digital display 16 which indicates the heart rate and a light 18 which flashes with each heartbeat. The front panel further includes an alarm reset button 20, the dials and controls 22 and 24 for setting the upper and lower limits for the alarm and a push-pull, rotary control knob 26 which serves the double function of setting the volume of an audible alarm as well as controlling the illumination display 16 and light 18. The latter provides a nighttime operating feature of the unit designed to eliminate patient annoyance with the unit especially at nighttime. As will be described in detail forthwith, this feature permits the display lights to be turned off and remain off as long as the patient's body is functioning properly. In the event of an alarm condition, both the lights and the audible alarm automatically activate.

As will also be described in detail forthwith, the display 16 is adapted to produce a 3-digit readout of the physiological function being monitored. In addition, the display is adapted to be driven to form the following mnemonics indicative of the condition of the patient or monitoring device: HI, LO, and OFF. The HI and LO signals flash intermittently with a numeric reading of the physiological function and their value is determined by the setting of controls 22 and 24. Thus, for example, if a high limit of 120 is set and exceeded, the mnemonic HI will flash intermittently with an actual reading of the heart rate which, at some later time, could still be above or possible below 120.

The OFF signal appears in the event of a malfunction in the patient sensor as for example, if the patient electrode lead falls off him. Other mnemonics may be provided for particular physiological function. Thus, a respirator monitor could be adapted to indicate if the patient monitored goes into an apnea condition by producing a suitable mnemonic such as "AP".

Referring to FIG. 2, a simplified block diagram for the present physiological function monitor circuit 28 is shown. The circuit includes a function detector circuit 30 which is shown in more detail in FIG. 3. In the present example of a heart rate monitor, the detector 30 detects the QRS of a patient's heartbeat. The inputs to the detector 30 are an ECG signal which is fed on line 32 and a BLANKING− input fed on line 34. In the following description, a minus sign after a signal (e.g., BLANKING−) indicates an active negative-going signal. The BLANKING− signal serves to momentarily blank the ECG signal which would be required to prevent inadvertent triggering of the alarms if a patient had a pacemaker and pacemaker pulses were being delivered to the patient.

The QRS detector 30 accepts a suitably amplified patient EDG input and converts it to a DC level output proportional to the input heart rate as will be described forthwith. It also generates an R-pulse output, coincident with each R-wave, which is fed through line 36 to flash the indicator light 18 on display panel 12 and through line 38 to speaker 40 to produce an audible "beep".

The DC output of detector 30 is fed through line 42 to an analog to digital converter 44 which serves to provide a 7-segment output signal to drive the display 16 which comprises three gas discharge digit indicators visible through the front panel 12.

The DC output of detector 30 is also fed on line 48 to an alarm generator circuit 50. The alarm generator 50 compares the DC level of the QRS detector with fixed inputs 52 determined by the setting of control knobs 22 and 24. In the event the DC level on line 48 does not fall within the permissible bounds determined by the settings of controls 22 and 24, the alarm generator 50 generates an alarm signal which is fed on line 54 to the character generator 56 and on line 58 to the audible alarm 40. The alarm generator 50 also has an ALARM INHIBIT− input through line 60. This input is in effect a fault detector which recognizes a fault indication such as a lead being off the patient. This signal causes the alarm signals to be inhibited which causes the character generator to drive the display to read OFF.

The character generator 56 receives the output of the alarm generator 50 through line 54 and generates suitable 7-segment output signals through line 62 and 64 to drive the display 16 to produce the mnemonic HI or LO indicative of the alarm condition or OFF indicative of the alarm inhibit condition.

A somewhat more detailed description of the above general description of the various blocks will now follow.

QRS Detector

As stated, the QRS detector 30 converts the EC input from the patient to a DC voltage proportional to the patient's heart rate and generates an R-pulse signal coincident with each R-wave. The circuitry utilized in fairly common and employed in existing digital monitoring equipment such as that heretofore available from the Electrodyne Division of Becton, Dickinson and Company of Sharon, Massachusetts, assignee of the present invention.

The QRS complex input on line 32 is fed to a unity-gain slew rate limit circuit 66 which limits the rate of change of the input signals. The output of circuit 66 is fed through a band pass filter 68 to a full wave rectifier circuit 70. The band pass filter circuit 68 includes a low pass filter, the gate of which can be adjusted by control 72 to allow the detector sensitivity to be varied. The band pass filter 68 further includes a high pass filter which, together with the low pass filter, comprises an inverting band pass filter which filters the R-wave from the QRS complex. A further input to the band pass filter 68 is the output of blanking circuit 74 which, in turn, receives a BLANKING− signal on lead 34 to blank the input to the band pass filter when a pacer blanking signal is present on lead 34. This prevents pacemaker pulses from triggering the detector.

The filtered R-wave output of rectifier 70 is fed to a peak detector 76 and comparator 78 to trigger a one-shot 80 that provides the R-pulse signal for driving the QRS indicator lamp 18 and audible alarm 40 on lines 36 and 38 respectively. The output of the one-shot is also attenuated and fed to a 3-pole filter 82 which converts the attenuated pulse to a DC voltage directly proportional to the rate of pulses. This DC voltage is applied through lines 42 and 48 respectively to the analog to digital converter 44 as well as the alarm generator 50.

Analog/Digital Converter

Figure 4:
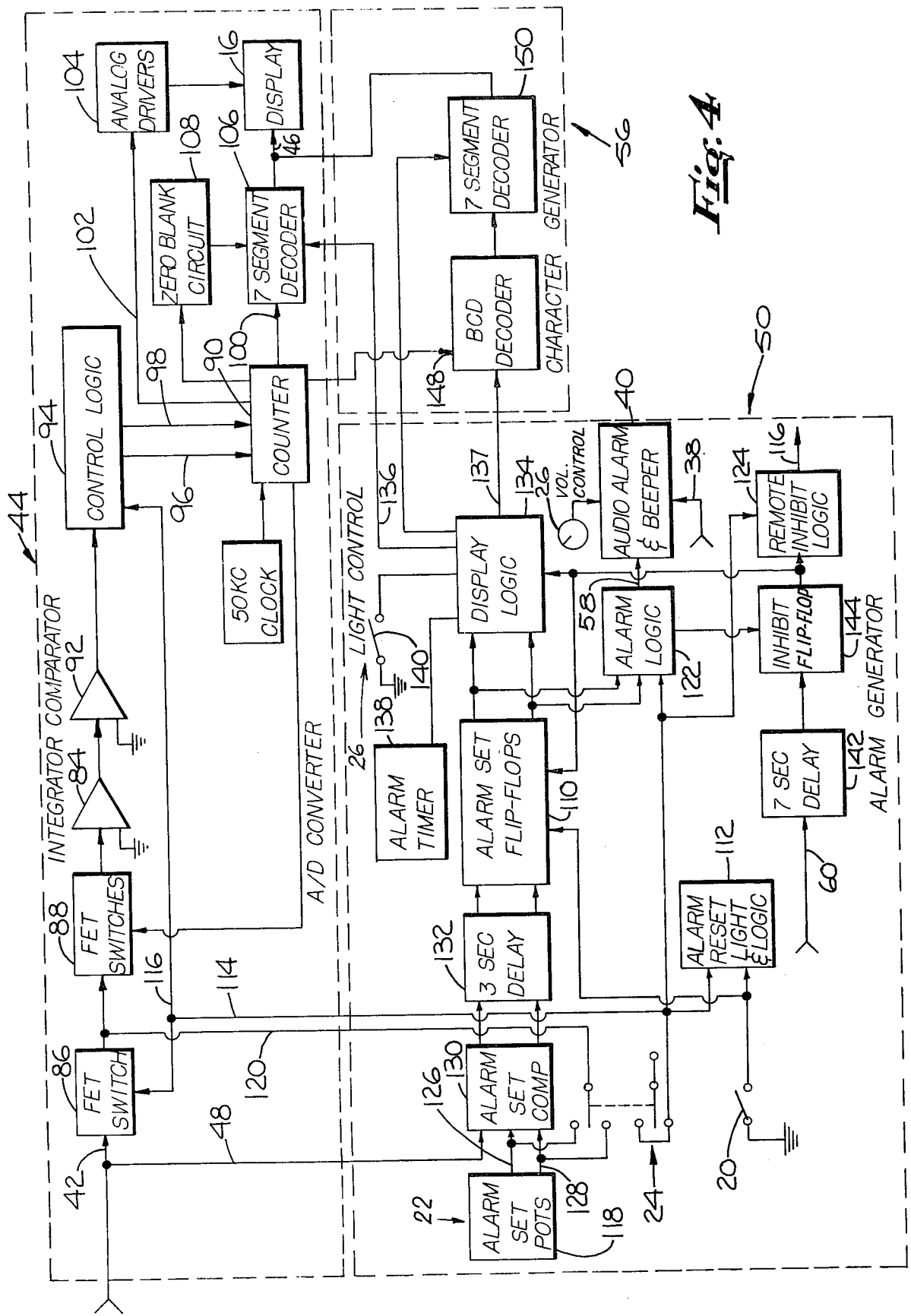
FIG. 4 is a more detailed view of various other blocks of FIG. 2.

The analog/digital converter 44 shown in detail in FIG. 4 is also of conventional design. The A/D converter receives the DC output of the QRS detector circuit on line 42 and converts it into 7-segment digital form for driving the display 16. To this end, a DC signal is applied to integrator 84 through FET switches 86 and 88. Switch 86 is normally kept on and switch 88 is kept on by counter 90 until the counter counts to 10,000 which is equal to a fixed time interval of approximately 170 ms. During this interval, the output of integrator 84 ramps to a negative value proportional to the DC input. On a 10,000 count, switch 88 switches to apply a voltage to the integrator driving its output to zero. When the output of integrator 84 crosses zero, comparator 92 switches states producing a pulse which, through control logic 94, generates a reset signal which is fed to counter 90 on line 96 after a 60 μs delay. The reset pulse restarts the counter so that the integration cycle is repeated.

The output of comparator 92 is also used to clock a 4-stage binary counter stage of control logic 94 which, together with a coder, generates one pulse for every 16 integration cycles. The positive edge of this pulse is used to generate a transfer pulse which transfers the count, which corresponds to the time required for the integrator output to ramp up to zero, into four storage latches within counter 90 through line 98. This count is directly proportional to the input heartbeat rate fed into the QRS detector 30 on line 32.

An internal scan oscillator in counter 90 sequentially transfers the count in the storage latches, scanning from the most significant digit to the least significant digit, to the binary coded decimal outputs 100 of the counter. The internal oscillator also generates a digit select output 102 corresponding to a selected latch. This turns on appropriate switches in the analog driver 104 so that a voltage is applied to the selected digit of display 16. The binary coded decimal outputs 100 from counter 90 are applied to the numeric display driver 106 where they are decoded into 7-segment high voltage outputs for driving the cathodes of the display. A zero blanking circuit 108 interposed between counter 90 and decoder 106 blanks the leading zeros until the first non-zero number or least significant digit occurs.

Alarm Generators

The alarm generator 50 is also shown in detail in FIG. 4. The principal function of the alarm generator is to detect an alarm condition and to produce the signals that are used by the character generator 56 to drive the digital display to produce the HI and LO characters during the alarm condition and the OFF character during an alarm inhibit condition. The alarm generator also includes an audio alarm which sounds in the event of an alarm condition to call immediate attention to the unit. The alarm circuits are enabled by depressing the ALARM RESET switch 20 on the face of the unit. This serves to enable flip flops 110 and causes the alarm reset lamp 112 that appears on the face of the unit to turn on. To set the alarm limits, the alarm set toggle switch 24 is moved from a neutral center position to a SET HI or SET LO position. This results in producing the following conditions:

a. A gate within the control logic 94 of the analog/-digital converter 44 is enabled through lines 114 and 116 to switch the converter to a fast up-date mode;

b. Switch 86 is turned off thereby disconnecting the DC from the A/D input and the SET LO or SET HI potentiometer 118 is switched to the A/D input along line 120 so that the setting may be read on display 16.

c. The alarm logic 122 (described in detail forthwith) is inhibited so that all alarm conditions are inhibited;

d. The remote inhibit logic 124 (described in detail forthwith) is inhibited so that the digital remote display is disabled.

The alarms are set by varying potentiometers 118 by turning knob 22 on the front panel. The alarm set potentiometers are connected through lines 126 and 128 (low and high settings respectively) with comparators 130 which also receive the DC input signal along line 48 from the QRS detector 30. If the DC reference exceeds the HI set point, the output of the high comparator after a 3-second delay produced by delay circuit 132 sets an alarm HI flip flop 110 the output of which drives display logic 134 and alarm logic 122. Similarly, if the DC reference drops below the LO set point, the output of the low comparator sets an alarm LO flip flop 110. Since flip flops 110 can only be reset by depressing the RESET switch 20 the first to occur of a HI or LO signal will continue to drive the display logic 134 thereby providing a memory of the alarm condition even if that condition subsequently subsides or even swings to an opposite alarm condition. The alarm logic drives audio alarm 40 to generate a continuous tone. The alarm logic also overrides the volume control 26 for the audio alarm. That is, even though the volume during ordinary monitoring may have been turned down or off, under an alarm condition, the audio alarm sounds at a predetermined level.

The display logic 134 also receives an input from timer 138 which causes the display logic to alternate between a high and low state. During the high state, a blanking signal is sent to decoder 106 of the A/D converter on line 136 while the HI (or LO) generate signal is fed to the character generator on line 137. In the low state, no signal is fed to the character generator and decoder 106 is not inhibited so that display 16 alternates between displaying HI (or LO) and the QRS reading.

A display light switch 140 which is a push-pull function of the volume control switch 26 is also provided. This switch serves to connect the display logic 134 with ground when closed to produce a constant blanking signal for decoder 106 along line 136. In this manner, the display may be turned off as may be desired, for example, during nighttime operating where the display would otherwise annoy the patient and possible interfere with his sleep. It should be noted, however, that the setting of switch 140 would not interfere with either the display of the alarm condition (HI or LO) or the audio alarm in the event of an alarm condition.

The alarm generator 50 also receives an alarm inhibit signal along line 60. This signal, is generated, when for example, the ECG electrode is off the patient so that no ECG signal is being received. The alarm inhibit signal is fed through a 7-second delay circuit 142 to a flip flop 144 which is set by alarm logic 122 when an alarm signal is generated by flip flops 110. The output of flip flop 144 is fed to the display logic 134 to produce the necessary driving signal for the character generator so that OFF is displayed.

Character Generator

The character generator 56 is also shown in FIG. 4. The character generator accepts the output from display logic 134 and decodes it into the proper 7-segment outputs for displaying the HI, LO and OFF characters as required. To this end, the output of display logic 134 is fed through line 137 into a binary coded decimal decoder 148 which converts the output of the display logic into the binary coded decimal code required by the character display driver 150 to generate the 7-segment outputs which are fed to the display 16.

As stated, the present invention is disclosed herein in the context of a heartbeat rate monitoring module. With slight modification, the invention could be adapted to monitor some other desired physiological rate such as respiration or pulse.

Thus, in accordance with the above, the aforementioned objects are effectively attained.

What is claimed is:

1. In a physiological function monitor module of the type comprising: a physiological function rate detector circuit adapted to receive an input from a patient and convert the same to a DC voltage output signal proportional to the rate of the physiological function of the patient under consideration; an alarm generator connected to the output of the detector circuit, said alarm generator including means for comparing the DC voltage level of the detector circuit to a preselected level and generating an alarm signal in the event said DC foltage level deviates beyond permissible bounds from said preset level; a digital display; and an analog/digital converter connected to the output of said detector circuit in driving relationship with said digital display; the improvement comprising a character generator connected to the output of said alarm generator and connected in driving relationship to the digital display in parallel with the analog/digital converter whereby said character generator drives said digital display to indicate an alarm condition in the event an alarm signal is generated, said alarm generator is adapted to generate a first signal in the event said detector circuit output exceeds said first preselected voltage level and a second signal in the event said detector signal is below said second preselected voltage level, and memory means adapted to maintain the output signal of said alarm generator at the first to occur of said first signal or second signal in the event said detector output signal varies from a first level above said first preselected voltage level to a second level below said second preselected voltage level or vice-versa.

2. The module in accordance with claim 1 further comprising means for inhibiting said alarm generator in the event of a fault condition, said character generator being adapted to drive said digital display to indicate the condition in the event said alarm generator is inhibited.

3. The invention in accordance with claim 1 wherein said physiological function rate detector circuit comprises a QRS detector circuit including an ECG input and further comprising means for isolating the R-wave from said ECG input and said module further comprises an audio alarm connected to said R-wave isolating means.

4. The module in accordance with claim 1 further comprising circuit means for turning said display off as long as said physiological function remains within said permissible bounds and automatically turns said display on in the event an alarm signal is generated.

* * * * *